US00PP23749P2

(12) United States Plant Patent
Irie

(10) Patent No.: US PP23,749 P2
(45) Date of Patent: Jul. 16, 2013

(54) ***HYDRANGEA* PLANT NAMED 'BTI'**

(50) Latin Name: *Hydrangea macrophylla*
Varietal Denomination: BTI

(76) Inventor: Ryoji Irie, Kyoto (JP)

( * ) Notice: Subject to any disclaimer, the term of this patent is extended or adjusted under 35 U.S.C. 154(b) by 14 days.

(21) Appl. No.: 13/385,361

(22) Filed: Feb. 15, 2012

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* named 'BTI' that is characterized by its mophead inflorescences with double sterile flowers that range in color from yellow-green to light pink to dark pink as they mature and may have inflorescences of different ages and colors on the plant simultaneously, its lack of fertile flowers, its large dark grey-green leaves, its height of about 50 cm, its rigid, strong stems that are dark red purple in color, and its continuous bloom from early April to September.

2 Drawing Sheets

Botanical classification: *Hydrangea macrophylla.*
Varietal denomination: 'BTI'.

BACKGROUND OF THE INVENTION

The present invention relates to a new and distinct cultivar of *Hydrangea macrophylla* and will be referred to hereafter by its cultivar name, 'BTI'. 'BTI' represents a new big leaf *Hydrangea*, a deciduous shrub grown for use as an ornamental landscape plant.

'BTI' was discovered by the Inventor as a naturally occurring branch mutation of 'RIE 05' (U.S. Plant Pat. No. 18,508) that was growing in a container at his nursery in Kyoto, Japan in 2008.

Asexual reproduction of the new cultivar was first accomplished by the Inventor using softwood stem cuttings in Kyoto, Japan in 2008. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'BTI' as a unique cultivar of *Hydrangea macrophylla.*

1. 'BTI' exhibits mophead inflorescences with double sterile flowers that range in color from yellow-green to light pink to dark pink as they mature and may have inflorescences of different ages and colors on the plant simultaneously.
2. 'BTI' exhibits inflorescence that lack fertile flowers.
3. 'BTI' exhibits large dark grey-green leaves.
4. 'BTI' reaches a height of about 50 cm.
5. 'BTI' exhibits rigid, strong stems that are dark red purple in color.
6. 'BTI' blooms continuously from early April to September.

'BTI' differs from its parent plant, 'RIE 05', in having longer stems that are dark red purple in color. 'BTI' can also be compared to the cultivars 'FREEDOM' (U.S. Plant Pat. No. 20,1046) and 'PERFECTION' (U.S. Plant Pat. No. 20,1047) and 'PEACE' (U.S. Plant Pat. No. 20,1016) as they are all similar in having double sterile flowers and in having a long blooming season. 'FREEDOM' differs from 'BTI' in having lighter pink flowers and in having green flowering stems. 'PERFECTION' differs from 'BTI' in having green flowering stems that are shorter in length. 'PEACE' differs from 'BTI' in having white flowers and in having green flowering stems that are shorter in length.

BRIEF DESCRIPTION OF THE DRAWINGS

The accompanying colored photographs illustrate the overall appearance and distinct characteristics of the new *Hydrangea* as grown in a greenhouse in De Kwakel, The Netherlands. The photographs were taken of one year-old plants of 'BTI' as grown in a 2-liter container.

The photograph in FIG. 2 provides a view of a maturing inflorescence of 'BTI'.

Figure 1:
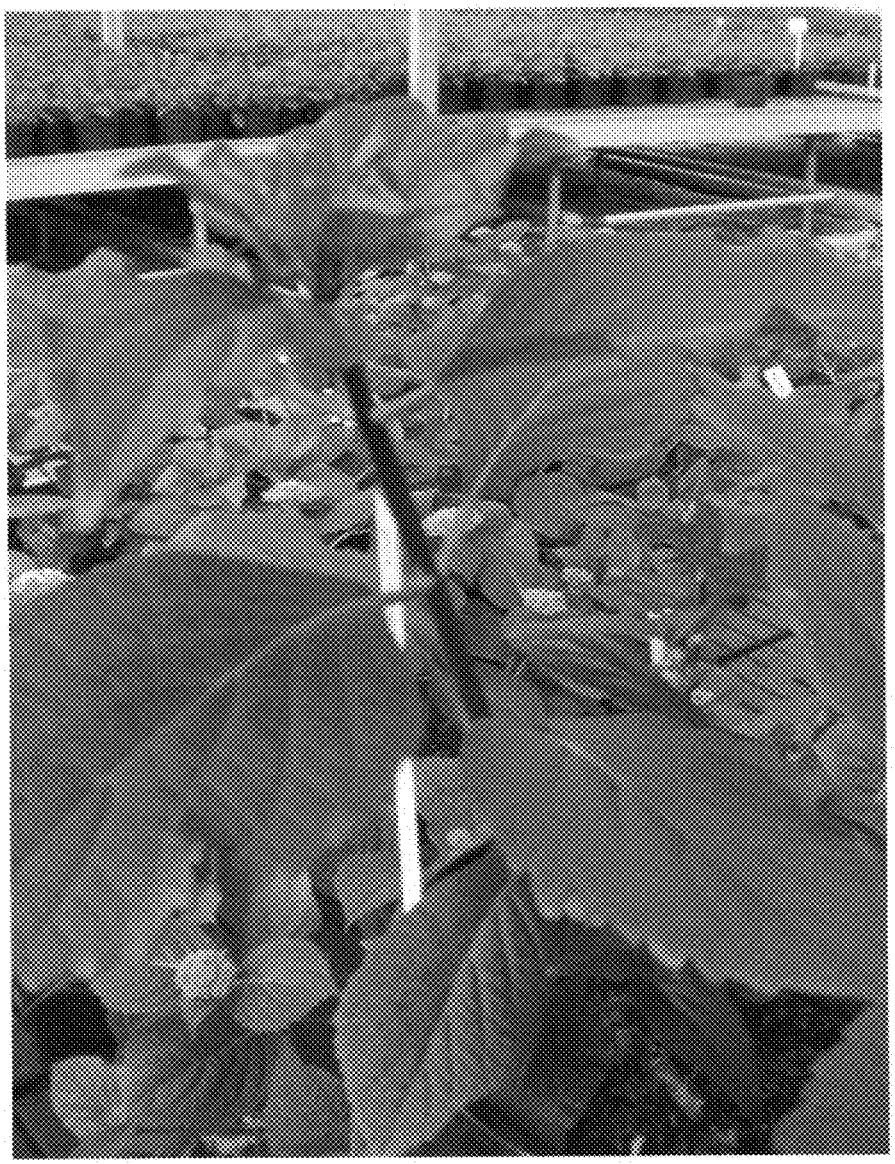
Figure 2:
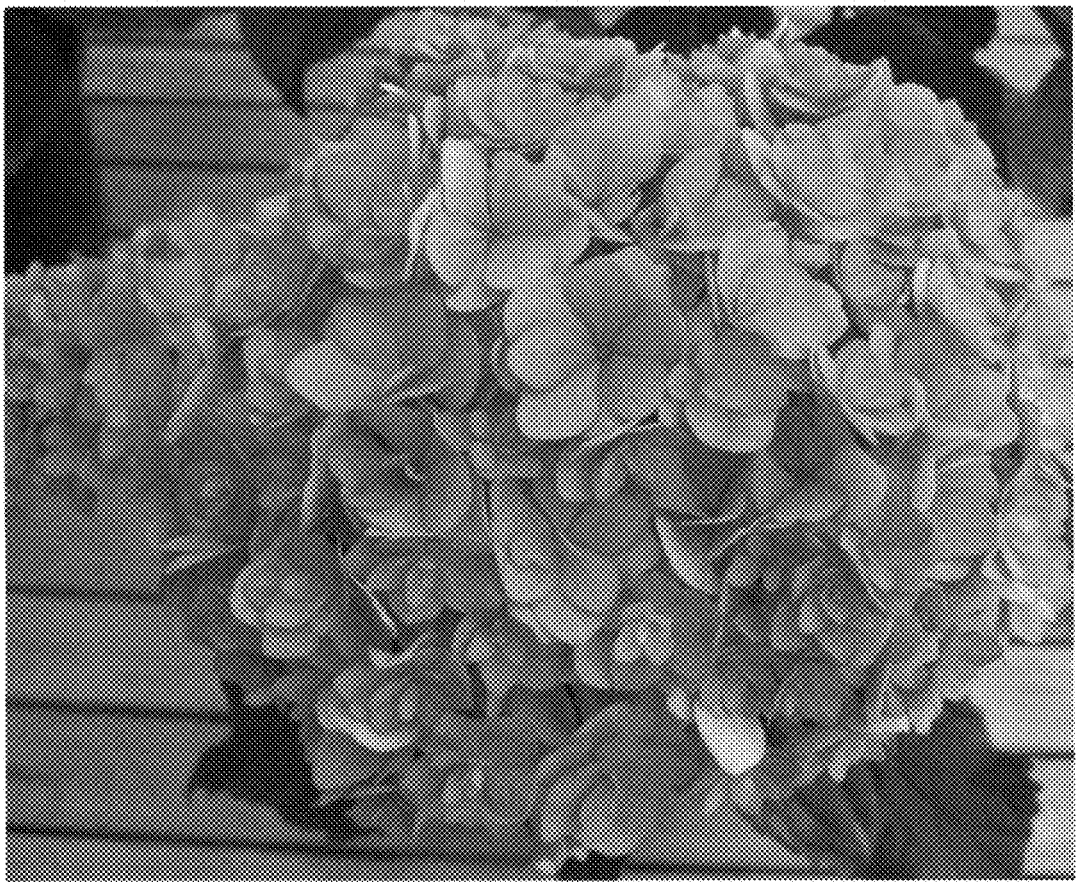

The photograph in FIG. 1 provides a close-up view of the foliage and a stem of 'BTI'.

The colors in the photographs may differ slightly from the color values cited in the detailed botanical description, which accurately describe the colors of the new *Hydrangea.*

BOTANICAL DESCRIPTION OF THE PLANT

The following is a detailed description of one year-old plants of 'BTI' as grown in a greenhouse in 2-liter containers in De Kwakel, The Netherlands. Phenotypic differences may be observed with variations in environmental, climatic, and cultural conditions. The color determination is in accordance with The 2001 RHS Colour Chart of The Royal Horticultural Society, London, England, except where general color terms of ordinary dictionary significance are used.

General description:

*Blooming period.*—April to September in De Kwakel, The Netherlands.

*Plant type.*—Deciduous shrub.

*Plant habit.*—Broadly upright.
*Height and spread.*—Reaches about 50 cm in height and 40 cm in diameter.
*Hardiness.*—At least in U.S.D.A. Zone 7.
*Diseases resistance.*—No susceptibility to pests or disease known to the inventor.
*Root description.*—Fine.
*Propagation.*—Softwood stem cuttings.
*Growth rate and vigor.*—Moderate.

Stem description:
*Stem shape.*—Round.
*Stem strength.*—Strong.
*Stem color.*—187A.
*Stem size.*—Average of 40 cm in length, and an average of 6 mm in diameter.
*Lenticels*.—An average of 8 per cm of stem surface, 2 mm in length; 0.5 mm in width, 187A in color.
*Stem surface.*—Slightly glossy.
*Internode length.*—An average of 5 cm.
*Branching*.—Moderate to sparse basal branching, pinching encourages lateral branching, average of 5 lateral branches on a one year-old plant.

Foliage description:
*Leaf shape*.—Leaves range from broad oval to elliptic-oblong.
*Leaf arrangement.*—Opposite.
*Leaf division.*—Simple.
*Leaf number.*—Average of 10 individual leaves per stem.
*Leaf base.*—Attenuate.
*Leaf apex.*—Apiculate.
*Leaf margins.*—Crenate.
*Leaf venation.*—Pinnate, upper and lower surface; between 144A and 146D.
*Leaf size.*—An average of 10.8 cm in length and 6.8 cm in width.
*Leaf attachment.*—Petiolate.
*Leaf surface.*—Smooth, slightly glossy on upper and lower surface.
*Leaf color.*—Young foliage upper surface; 139A, mature upper surface; 147A, young and mature foliage lower surface; 137C.
*Petioles.*—Average of 2.2 cm in length and 3 mm in diameter, 144A in color, round in shape, glabrous surface.

Inflorescence description:
*Inflorescence type.*—Terminal compound corymb, mophead in form and comprised double sterile flowers, lacks fertile flowers.
*Lastingness of inflorescence.*—Persistent.
*Inflorescence number.*—One per lateral or sublateral stem if pinched.
*Inflorescence size.*—Average of 11.5 cm in height and 13 cm in width.
*Flower number.*—An average of 250 flowers.
*Flower fragrance.*—None.
*Flower aspect.*—Upright or outward on corymb, flowers cupped rather than flat.
*Flower size.*—Average of 2.8 cm in diameter and 1.2 cm in depth.
*Flower type.*—Rotate.
*Flower buds.*—An average of 5.5 mm in length and 2 mm in width, ovate in shape, obtuse apex, 145C in color.
*Peduncles.*—Moderately strong, average of 5.1 cm in length and 3.5 mm in width, average angle of 40° from vertical, 144A in color, lenticels present; 2 mm in length, 0.3 mm in width, 187B in color.
*Pedicels.*—Held at a 35° angle from vertical, moderate strength, average of 7 cm in length and 1 mm in width, 64B in color, glabrous surface.
*Petals.*—Only petal spot present, about 2 mm in diameter, matures to 70B in color.
*Sepals.*—An average of 12, up to 1.4 cm in length and up to 1.2 cm in width, dull and glabrous on upper and lower surface, unfused, rhomboidal to broadly elliptic in shape, entire margin, rounded to broadly acute apex, color upper and lower surface when opening; 149C, color when fully open upper surface; a blend of 62C and 62D, color when fully open lower surface; 62D with veins 63D, color when mature upper surface; color between N66C and 70B, color when mature lower surface; 75B with veins 75A.

Reproductive organs: None observed, no fertile flowers were observed.

It is claimed:

1. A new and distinct cultivar of *Hydrangea* plant named 'BTI' substantially as herein illustrated and described.

* * * * *